United States Patent [19]

Neri et al.

[11] 4,154,957

[45] May 15, 1979

[54] METHOD FOR THE PREPARATION OF ESTERS

[75] Inventors: Carlo Neri; Antonio Esposito, both of San Donato Milanese, Italy

[73] Assignee: Anic S.p.A., Palermo, Italy

[21] Appl. No.: 756,646

[22] Filed: Jan. 4, 1977

[30] Foreign Application Priority Data

Jan. 9, 1976 [IT] Italy .............................. 19095 A/76

[51] Int. Cl.$^2$ ...................... C07C 67/05; C07C 69/16; C07C 69/18
[52] U.S. Cl. ................................... 560/246; 560/263
[58] Field of Search ...................... 260/488 J, 497 R; 560/246, 263

[56] References Cited

U.S. PATENT DOCUMENTS 2,316,604  4/1943  Loder et al. ...................... 260/497 R
4,009,203  2/1977  Schmerling .......................... 560/247

*Primary Examiner*—Vivian Garner
*Attorney, Agent, or Firm*—Morgan, Finnegan, Pine, Foley & Lee

[57] ABSTRACT

A method is disclosed for preparing esters by reacting an olefin with an acid in the presence of oxygen and a catalyst system, the improvement consisting in that the catalyst system is a compound of tin or cerium, used in the presence of iodine or of a iodine-yielding compound. High productivities are achieved and no pollution problems are to be solved.

5 Claims, No Drawings

METHOD FOR THE PREPARATION OF ESTERS

This invention relates to a method for the preparation of esters, starting from compounds which contain at least an ethylenic unsaturation, which are reacted with the relevant acid and with oxygen in the presence of an appropriate catalyst system.

It is known that esters can be obtained by reacting olefins with acids in the presence of oxygen, but the catalyst systems adopted hitherto are not exempt from drawbacks.

For example, the Belgian Pat. No. 803189 relates to the use of a catalyst system formed by tellurium or selenium coupled with chlorine or bromine. Even though the results are satisfactory, the metals mentioned above have, however, a rather high cost, that which has a bearing on the economy of the entire process and are such as to introduce considerable toxicity problems. In addition, the reaction is limited by the fact that certain conditions must be scrupulously observed, such as temperature and pH.

The possibility is likewise known of employing, in the reaction aforementioned, a catalyst system as formed by an iodide and by a transition metal selected from those having an atomic number of less than 48. This catalyst system, however, does not permit to reaching high values of hourly outputs, unless the working temperatures adopted are high, which is still a serious handicap when the reaction is regarded from an industrial point of view. The present Applicants have now ascertained, which is the subject-matter of the present invention, that it is possible to prepare esters starting from compounds containing at least one ethylenic unsaturation, with a high output even at comparatively low temperatures and without raising problems with respect to environmental pollution, by reacting the unsaturated compound with the acid and oxygen in the presence of a catalyst system which is formed by tin or cerium in the presence of iodine or any compound capable of setting iodine free.

The reaction takes place independently of the working conditions, although it is preferred to work at temperatures over 80° C. and, more particularly, at temperatures in the range from 100° C. to 180° C. The pressure, in its turn, does not influence in any wise the reaction run and it will be possible to work with values of pressure near the atmospherical value and, anyhow, always below 50 atmospheres for practical reasons.

The respective amounts of olefins and oxygen which are caused to react can be selected over wide ranges, from an excess of the olefin, to an excess of oxygen. It will be obviously preferred to work in the presence of an excess of oxygen to prevent the formation of explosive mixtures. The quantity of the acid, conversely, is not critical, inasmuch as the acid may also act as the reaction solvent.

The reaction in fact, can take place in the liquid phase and the diluent can be, as outlined above, the acid as such, or any other inert solvent: on the other hand, the acid can play a role in the reaction in the form of an anion of the metal which belongs to the catalyst system, that is, tin or cerium. This is the case of a batchwise run, since, otherwise, the reaction takes place in a continuous run, on account of the regeneration of the iodine or the metallic salt by the action of oxygen.

All the working details will become clear from consideration of the ensuing illustrative examples, which are by no means to be construed as limitations of the invention, since the working ranges can either be amplified or changed consistently with that which has been indicated hereinabove.

EXAMPLE 1 TO 4

A polytetrafluoroethylene-coated stainless steel autoclave, equipped with a magnetic stirrer, is charged with 50 grams of glacial acetic acid, 1 millimol of SnO (135 milligrams) and 6 millimols of iodine (760 milligrams). A mixture of an olefin and oxygen in the volume ratio of 1 to 2.5 is charged under a pressure of 15 atmospheres. The autoclave is immersed in a thermostatically controlled bath at 150° C. and stirring is started. The pressure attains 25 atmospheres and is maintained at such magnitude by allowing for the consumption with the introduction of olefin-oxygen mixture. After 6 hours of reaction, the solution is chromatographed and yield and selectively are measured. The results are reported in the following table:

| Olefin | Diacetate millimols | Monoacetate millimols | Selectivity % |
|---|---|---|---|
| Ethylene | 65 | 25 | 97 |
| Propylene | 75 | 20 | 98 |
| Butene-2 | 80 | 15 | 96 |
| Allyl alcohol | 60 | 15 | 95 |

Selectivity is calculated relative to the olefin which has been consumed and on taking into account the sum of the diacetate and the possible monoacetates.

EXAMPLES 5 TO 8

The procedure is the same as for Examples 1 to 4 above, but the temperature is 125° C. The selectivity is the same as for the previous cases, whereas the conversions fall by about 20% with respect to the previous values.

EXAMPLES 9 TO 12

The procedure is the same as for Examples 1 to 4, but 25 grams of acetic acid and 25 grams of acetic anhydride are used. No monoacetate is formed, but conversion and selectivity do not change appreciably.

EXAMPLES 13 TO 16

The procedure is the same as for Examples 1 to 4, but 25 grams of acetic acid and 25 grams of water are used. Conversion and selectivity do not change, but there is a predominant formation of monoacetates.

EXAMPLES 17 TO 20

The procedure is the same as for Examples 1 to 4, but the overall working pressure is 5 atmospheres. No substantial changes in selectivity and conversion are experienced.

What we claim is:

1. The method of preparing an ester which comprises, reacting a compound selected from the group consisting of ethylene, propylene, butene-2 and allyl alcohol, with oxygen and acetic acid in the presence of a catalyst composed of SnO and iodine.

2. The method of preparing an ester as claimed in claim 1, wherein the temperature at which the reaction is conducted is over 80° C.

3. The method of preparing an ester as claimed in claim 2, wherein the temperature at which the reaction is conducted is in the range between 100° C. and 180° C.

4. The method of preparing an ester as claimed in claim 1, wherein the reaction is carried out under a pressure below 50 atmospheres.

5. The method of preparing an ester as claimed in claim 1, wherein the reaction is carried out with an excess of oxygen.

* * * * *